United States Patent [19]
Telmissani

[11] Patent Number: 6,030,838
[45] Date of Patent: Feb. 29, 2000

[54] HEMATOLOGICAL PARAMETER

[75] Inventor: Omar A. Telmissani, Dahram, Saudi Arabia

[73] Assignee: EMT & Associates, Inc., New York, N.Y.

[21] Appl. No.: 09/159,632

[22] Filed: Sep. 24, 1998

[51] Int. Cl.$^7$ ................................................ G01N 33/48
[52] U.S. Cl. ................................ 436/63; 436/8; 436/66; 435/2
[58] Field of Search .................................. 436/8, 15, 10, 436/63, 66; 435/2

[56] References Cited

U.S. PATENT DOCUMENTS

| | | | |
|---|---|---|---|
| 4,097,845 | 6/1978 | Bacus | 382/134 |
| 5,059,395 | 10/1991 | Brittenham et al. | 422/73 |
| 5,194,909 | 3/1993 | Tycko | 356/40 |
| 5,705,739 | 1/1998 | Levine et al. | 73/61.72 |

OTHER PUBLICATIONS

Bacus et al. *Journal of Histochemistry & Cytochemistry*, vol. 25 (7), pp. 614–632. (abstract), Jul. 1977.

Bessman et al. "Quantitative anisocytosis as a discriminant between iron deficiency and Thalassemia Minor" *Blood* 53:288–293, Feb. 1979.

England et al. "Differentiation of iron deficiency from Thalassaemia Trait by routine blood–count". *The Lancet* Mar. 3, 1973, 499–453.

England et al. "Differentiation of iron deficiency from Thalassaemia Trait." *The Lancet* Jun. 30, 1973.

Shine et al. "A strategy to detect B–Thalassaemia Minor". *The Lancet* Mar. 20, 1977, pp. 692–694.

Mentzer "Differentiation of iron deficiency from Thalassaemia Trait". *The Lancet* Apr. 21, 1973, p. 882.

Fairbanks et al. "CH2. The Anemias In Manual of Clinical Hematology" F.F. Mazza, ed. Little, Brown Boston, New York, Toronto, London, pp. 26–27, date unknown.

England et al. "Discrimination between iron–deficiency and heterozygous–Thalassaemia syndromes in differential diagnosis of micro–cytosis". *The Lancet*, Jan. 20, 1979, pp. 145–148.

Aembroushi et al. "CH 4: Quality control and Statistics." In Bishop et al. (eds.) In Introduction to Clinical Chemistry, pp. 68–75, date unknown.

Fleming et al. Brief Critical Reviews "Plasma transfer receptor . . . " Nutrition Reviews 53(6):167–175, Jun. 1995.

Walford et al. "Discrimination between iron deficiency and heterozygous Thalassaemia", date unknown.

Mohandas, et al. "Accurate and independent measurement of volume and hemoglobin concentration of individual red cells by laser scattering." *Blood* § § : 506 (1986).

Mohandas, et al. "Automated quantitation of cell density distribution and hyperdense cell fraction in rbc disorders" *Blood* § 74 : 442 (1989).

*Primary Examiner*—Maureen M. Wallenhorst
*Attorney, Agent, or Firm*—White & Case LLP

[57] ABSTRACT

A new hematological parameter, namely mean hemoglobin density in one liter of blood (MDHL), is based on the new index of mean cell density of hemoglobin, MCHD, or more particularly, MDHL is provided as an advantageous screening parameter to distinguish between Iron Deficiency Anemia (IDA) and Thalassaemia Trait TT. The MDHL parameter showed superior sensitivity, specificity, predictive value and efficacy of as high as 100%. The new screening test also entails significantly lower costs involving the evaluation of patients with hypochromic microcytosis.

7 Claims, No Drawings

HEMATOLOGICAL PARAMETER

FIELD OF THE INVENTION

The invention is related to a novel screening parameter for hypochromic microcytosis, or more particularly a parameter based on a new red blood cell index for distinguishing between an iron deficiency anemia and a Thalassemia Trait.

BACKGROUND OF THE INVENTION

Within this application several publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

Iron deficiency anemia (IDA) and Thalassemia Trait (TT) are the common causes of hypochromic microcytosis. Differentiation between these diseases is based on the measurement of serum iron, total iron binding capacity and/or the serum ferritin for IDA; and when the iron status is normal, estimation of Hb fractions, by electrophoresis for example, is required for TT. However, these procedures are complicated and expensive, especially when, in addition, alpha ($\alpha$) Thalassemia Trait ($\alpha$-thal) is considered. In some cases, it may require globin chain synthesis rate determination or even $\alpha$ globin gene analysis.

Hematological analysis has been relying on the red blood cell (RBC) indices which were first introduced by Wintrobe[1] in 1929. These include the mean corpuscular or cell volume (MCV), mean corpuscular or cell hemoglobin (MCH) and mean corpuscular or cell hemoglobin concentration (MCHC). MCV is an estimate of the average RBC volume expressed in femtoliter (fl) or $10^{-15}$ L, whereas MCH is a real quantity, where the hemoglobin (Hb) content of the average red blood cell[2] is expressed in picograms (pg) or $10^{-12}$ g. MCHC is defined as the hemoglobin concentration in the average RBC, that is understood to be the amount of Hb within the average RBC volume in which it is contained.[2] The MCHC value is calculated by dividing Hb concentration of blood (grams/liter) by the hematocrit value (liter/liter). MCHC is usually reported in grams/liter (g/L) or grams/deciliter (g/dl)[3].

The MCHC index has been widely accepted as a "natural" constant, not only in man but also elsewhere in the animal kingdom. Furthermore, this value varies very little even under pathological conditions. Therefore, a drastic diminution of concentration by say 30%, such as would be caused by severe iron deficiency is regarded as highly significant. Since Wintrobe, several different formulae have been introduced to discriminate between blood iron deficiency and Thalassemia Minor.

England and Fraser[4,5] proposed a linear Discriminant Function (DF) derived from the Mean Corpuscular Volume (MCV), Red Blood Corpuscle (RBC), and hemoglobin (Hb) concentration. Accordingly, the equation for DF is MCV−RBC−(5×Hb)−k, where k is a constant determined by the method used to calibrate the cell counter: Positive DF values are alleged to indicate IDA and negative values, TT. Mentzer[6] proposed that simple index derived from the ratio, MCV/RBC, was also capable of distinguishing the two conditions, with values below 13 indicating TT. Shine and Lal[7] introduced the expression $(MCV)^2 \times MCH$ (Mean Cell Hemoglobin) to screen for TT, where values of less than 1530 were regarded as diagnostic of this condition. Another formula is the Discrimination Score (DS),[8] based on the expression (0.096×MCV)+(0.415×RDW)−(0.139×RBC)−12.722 for the male, and the expression (0.096×MCV)+(0.415×RDW)−12.722 for the female, with 0.3095 as cutoff point, below which TT is probable and above which IDA is considered likely.

However, all of the above approaches have significant limitations. Firstly, their incorporation in CBC hemogram is impractical because the mathematical procedures are elaborate and apply only to one category of RBC changes. Secondly, the sensitivity and specificity of the calculations are not high, resulting in significant imprecision in discriminating between IDA and TT. Accordingly, there is still a need for a simple and effective way to discriminate between these conditions.

Therefore it is an object of this invention to provide new parameters for the determination of the average amount of hemoglobin per red corpuscle. It is another object of this invention to use the new parameters for screening RBC, which would provide useful information more directly and simply from the hematology data picture of a patient for the differentiation between IDA and TT.

SUMMARY OF THE INVENTION

It has now been found that a redefinition of Wintrobe's index, MCHC, in terms of density of hemoglobin rather than concentration, affords an index of the amount of hemoglobin per average red blood cell in units of picograms/femtoliter (pg/fl). Moreover, this newly defined index of mean corpuscular hemoglobin density has been found to be effective in the evaluation of the common clinical hematology problem of hypochromic microcytosis and especially in the calculation of a new discriminant function for IDA and TT.

In accordance with the invention, the new RBC index, MCHD, is defined as the Mean Hemoglobin Density per single RBC, which number is derived from the ratio, MCH (pg)/MCV (fl), as defined above. Therefore, MCHD has the units: pg/fl. Further to this invention, it has been discovered that MCHD affords an effective discriminant function for IDA and TT. Specifically, the discriminant function is a new parameter which is defined the Mean Density of Hemoglobin in one liter of peripheral blood, or MDHL. More specifically, the parameter of RBC, MDHL is related to MCHD by the product of MCHD (pg/fl)×RBC×($10^{12}$/L) in grams per one liter (g/L) of blood.

The preferred embodiment in accordance with the invention is found very useful in that the new discriminant function MDHL affords a new blood screening test of very high reliability, sensitivity and efficacy. In particular, reliability and sensitivity of the discriminant function of MDHL is found close to or/at 100% for either IDA or TT.

The screen test for IDA and TT can be calculated by the following equation MDHL (g/L)=MCH/MCV×RBCC×$10^{12}$/L, where RBCC is red blood cell count.

The newly defined RBC indices are useful as a screen distinguishing IDA from TT since a MDHL parameter of HM blood which is lower than the normal median of MDHL will indicate an IDA condition, while a MDHL parameter of HM blood which is higher than the normal median of MDHL will indicate TT.

DETAILED DESCRIPTION OF THE INVENTION

Since peripheral blood Hb content is usually measured in units of g/L, MCHC as defined above appears to be a contradiction in terms. While MCHC is supposed to represent the average concentration of Hb within the average RBC in peripheral blood, it is a number derived from whole blood Hb values and the hematocrit (HCT) which is the volume to total blood sample occupied by red blood cells as a packed cell volume (PCV). For example, the average concentration of hemoglobin is described as 150 grams of Hb in one liter of blood (including plasma). However, the Wintrobe index appears based on a misconception of the Hb concentration. Concentration is well known as the quantity of a substance in terms of a weight, mole, or equivalent dispersed in the unit volume of another substance[9], frequently a liquid. For example, a saline solution is 9 g NaCl dissolved in one liter of water. In contrast, density is the amount of a substance in relation to the volume it occupies, i.e., as measured by the mass of a substance per unit volume occupied by the substance[10]. Examples for different physical density parameters, one could mention the x-ray density of iron (Fe) at 7.875 g/l and lead (Pb) at 11.35 g/l.[9] Regarding the conventional MCHC index, it is clear that blood is not a liquid per se but (inter alia) a suspension of red blood cells. Thus, hemoglobin is contained or bagged within each red blood cell.

Since red blood corpuscles or cells constitute a defined average volume occupied by Hb, it is misleading to refer to the content of the Hb in RBC as a concentration. The fact that a certain amount of Hb occupies a defined corpuscular volume of the average RBC would satisfy the definition of particular density of Hb in a RBC. Thus, the Wintrobe constant MCHC does not refer to a concentration of hemoglobin in blood but actually the amount of hemoglobin contained in the red blood cell volume. As defined by Wintrobe, the MCHC number is determined by dividing Hb concentration of the blood in grams/liter or grams/deciliter by the hematocrit value (liter per liter), where the hematocrit is the volume occupied by the red blood cells in a volume of blood.

However, the MCV index is obtained from the expression, hematocrit (L/L)×1000/red cell count×$10^{12}$/L such that the resulting unit is $10^{-15}$ L or femtoliters, and secondly, MCH is obtained from hemoglobin (g/L blood) divided by red cell count×$10^{12}$/L blood resulting in Hb concentration in pg contained in the average red blood cell. It is clear that the MCHC unit (g/L) is orders of magnitude different from the units of the MCV index (fl) and the MCH index (pg) in relation to one average red blood cell.

Therefore, the newly defined index MCHD has units of (pg/fl) which is more reasonable for providing a mean hemoglobin density per average red blood cell.

The density of hemoglobin in one red blood cell is by necessity an approximation, since the exact true quantity of hemoglobin would require complex and expensive analytical equipment.

The clinical usefulness of the invention was evaluated in comparison with the known methods for discriminating between IDA and TT. The methods and apparatus of forming the basis of the clinical data are described below. The efficacy of the new parameters MCHD and MDHL was determined by the following calculations from earlier blood tests. The patients, retrospectively selected for this reevaluation, were older than 12 years with a microcytic hypochromic blood picture as observed under the microscope, Hb greater than 70 g/l and MCV<80 fl, complete iron profile and Hb electrophoresis. The RBC of patients and normal subjects was performed on a STKS automated cell counter (Coulter Electronics, Hialeah, Fla). Quantification of serum iron was done on Boehringer Mannheim (BM)/Hitachi 917 Clinical Chemistry analyzer using the ferrozine method, while ferritin was assayed by a chemiluminescence sandwich assay on the Ciba-Corning ACS: 180. Transferrin was measured turbidimetrically on a Cobas Mira Plus/Unimate 3 system (Roche Diagnostics) and the iron binding capacity was calculated from the transferrin value (multiply g/L×24). Hemoglobin analysis was performed by hemoglobin electrophoresis on cellulose acetate membrane at pH of 8.4. Hemoglobin $A_2$ quantification was performed by ion exchange column chromatography using the Beta-Thal Quick column (Helena Laboratories, Beaumont, Tex.). Hemoglobin F was determined by radial immuno-diffusion method using a kit manufactured by Helena Laboratories. Diagnosis of beta thal (β-thal) trait was based on demonstrating an $HbA_2$ level higher than 3.7%, which is the upper limit of normal in this laboratory. The diagnosis of α-thal trait was based on demonstrating a normal $HbA_2$ level or one below 2.2%, which is a lower limit of normal, with or without the presence of HbH inclusions in RBC. Data for the normal reference range for peripheral blood RBC was obtained from a study by Al-Buhairan[12] performed on the same machine in the same institution.

For each set of patient and control data, MCHD was calculated from the relation MCH/MCV, and MDHL was calculated from the relation MCHD×RBCC as described above. The mean, median and standard deviation of MCHD and MDHL values were also calculated. The efficacy of the MDHL index discriminating between IDA and TT was compared with calculated values obtained from the aforementioned prior art formulae. The following cutoff points for the various discriminant procedures were taken as recommended in the prior art: For DF, positive values indicate IDA, whereas negative values indicate TT. For the $(MCV)^2$×MCH formula of Shine and Lal, values of less than 1530 would indicate TT. For the MCV/RBC ratio, values >13 allegedly indicate IDA, whereas those of <13 would indicate TT. For the DS, values >0.3095 are supposed to indicate IDA and those <0.3095 are supposed to indicate TT.

For the new MDHL parameter the cutoff point is the median value of normal blood, according to which IDA is a probable diagnosis if the MDHL value is below, and TT if it is above.

In addition, sensitivity and specificity were calculated according to standard formulae,[11] such that, Sensitivity=(TP)÷(TP+FN) and Specificity=(TN)÷(TN+FP), where TP=true positives, FN=false negatives, TN=true negatives and FP=false positives. The predictive values (PV), whether positive or negative, are similarly calculated, with the positive PV deriving from (TP)÷(TP+FP) and the negative PV deriving from (TN)÷(TN+FN). Finally, the efficacy of the discriminant function was calculated from the following relationship: (TP+TN)÷(TP+TN+FP+FN).

On the basis of the data from the study of Al-Buhairan[12] the MDHL according to this invention of normal male subjects showed a mean of 1.75±0.24 (±2 SD) and a median of 1.73; and the MTHD of normal females subjects showed a mean and a median of 1.50 ±0.21 (±2 SD) (Table 1).

TABLE 1

Normal Mean Cell Hemoglobin Density (MCHD) and
Mean Density Hemoglobin Per Liter of Blood (MDHL)

|  |  | Median | Mean | Standard Deviation |
|---|---|---|---|---|
| Male | MCHD | 0.339 | 0.340 | 0.006 |
| Female | MCHD | 0.339 | 0.339 | 0.006 |
| Male | MDHL | 1.73 | 1.75 | 0.12 |
| Female | MDHL | 1.50* | 1.50 | 0.11 |

The study population consisted of 96 adult patients of whom 49 were females. Using criteria outlined above, there were 43 patients with IDA and 53 with TT (Table 2). Of the 53 patients with TT, 35 had β-thal trait and the remaining 18 α-thal trait.

TABLE 2

Sex Distribution and Diagnoses of 96 Patients Studied.

|  | IDA | TT | TOTAL |
|---|---|---|---|
| MALE | 16 (1)* | 31 | 47 |
| FEMALE | 27 | 22 (2)** | 49 |
| TOTAL | 43 | 53 | 96 |

IDA: Iron Deficiency Anemia
TT: Thalassemia Trait
*: One patient with associated TT
**: Two patients with associated IDA The computation of the mean, the median and SD of the MDHL produced data which showed that patients with values below the median of normal subjects were most likely to have IDA (positive PV of 87.7%), whereas those patients whose MDHL was greater than the median were more likely to have TT (positive PV of 97.9%). When compared with the aforementioned prior art discriminant formulae, the new parameter, MDHL according to this invention, showed a significantly higher efficacy in the diagnosis of IDA and TT as compared to the others. These comparisons are summarized in Table 3. Although the $(MCV)^2 \times MCH$ formula is included in this comparative list, it is not strictly considered comparable with the others, since this formula is only intended for identifying Thalassemia patients, as originally described[6].

The new parameter, MDHL, and the blood index MCHD, have been found useful to rationalize the concepts of Hb distribution within the average RBC. The above-described reevaluation of the (CBC data) 96 of patients has demonstrated that the MCHD index is a more suitable for assessing the average content of Hb within the average RBC since it MCHD directly reflects as to the quantity contained in the single unit cell volume. The new parameter MDHL, which is derived from the MCHD, is a calculated estimate of the Hb dispersal in one liter of blood analyzed by the machine. In comparison to the well known conventional parameter MCHC by Wintrobe, the new index MCHD correctly identified the amount of Hb in terms of density per single RBC and fits advantageously by the relative scale of the unit fl or $\mu m^3$ of measurement; it differs from MCHC by a factor of $10^{12}$. Thus, the measurement units (pg/fl) of MCHD are more in line with the average size RBC units, and in harmony with MDHL.

Therefore, in view of the above-presented results, the advantage of MCHD is (i) which is an index based on a clearly defined concept and number; (ii) more directly related to a single RBC in terms of the units, pg/fl, and (iii) calculated from MCV results on which the diagnosis of microcytosis or macrocytosis is generally based.

Assuming that MCH the RBC-Hb is the index of color and MCHD is the RBC-Hb density index, it can be postulated that patients with microcytic, hypochromic and hypodense RBC indices would be suggested to have an IDA, whereas patients with microcytic, hypochromic and normodense RBC indices would have TT. In addition, patients with normocytic, normochromic and hyperdense RBC indices would be suggested to have Hereditary spherocytosis.

Finally, the results of calculations based on the new indices in accordance with this invention have been found as not significantly affected by the technical shortcomings in the measurements when the indices are evaluated for the purpose of differentiating between IDA and TT. The Coulter principle used in determining the MCHD in this study has limitations because true density of Hb is difficult to calculate and requires expensive apparatus. Alternative laser light scattering-based methods of measuring individual RBC Hb have been shown to be more accurate, but such information has not been presently applied to the problem of distinguishing between IDA and TT[11]. Moreover, RBC density is different from MCHD or MDHL because the cellular density of the whole RBC is estimated by other techniques, such as e.g. buoyancy gradient techniques or sedimentation rates. Thus, significant increases in cellular RBC density are observed in sickle cell syndromes and Hb CC[12]. The cellular RBC density has not been applied to distinguish between IDA and TT.

The parameters according to this invention were tested with regard to their clinical validity in the common hematological conundrum of differentiating between IDA and TT. For establishing the advantageous aspects of discrimination between IDA and TT by this inventive method, MDHL was evaluated for sensitivity, specificity, predictive value and efficacy, and as compared with the conventional discriminant formulae.

Using MDHL, in this reevaluation study of 96 patients, the results demonstrate that subjects with IDA have a MDHL lower than the median level of a normal reference population, whereas TT patients have a MDHL higher than the median. Seven patients, all females who had IDA and were under specific therapy, were correctly classified by a low MDHL. It is noted that, although the median MDHL provided a clear discriminator between IDA and TT in patients MDHL would not be useful for evaluating subjects with normal MCV and normal MCH because half of normal subjects must, by definition, have a lower MDHL, whereas the other half must have a higher MDHL.

As can be observed in Table 3, sensitivity, specificity, predictive value and efficacy were superior to those obtained with the other formulae.

TABLE 3

Comparison between the new blood parameter MDHL and the four reported formulae.

| | Sensitivity % | | Specificity % | | PV+ % | | PV− % | | Efficacy % | |
|---|---|---|---|---|---|---|---|---|---|---|
| | IDA | TT | IDA | TT | IDA | TT | IDA | TT | IDA | TT |
| MDHL | 97.7 | 88.7 | 88.7 | 97.7 | 87.5 | 97.9 | 97.9 | 87.5 | 92.7 | 92.7 |
| FORM 1 | — | 100 | — | 7.5 | — | 56.9 | — | 100 | — | 58.3 |
| FORM 2 | 95.3 | 83 | 83 | 95.3 | 82 | 95.6 | 95.6 | 82 | 88.5 | 88.5 |
| DS | 81.4 | 83 | 83 | 81.4 | 79.5 | 86.6 | 84 | 79.5 | 82.3 | 82.3 |
| DF | 97.7 | 73.6 | 73.6 | 97.7 | 75 | 97.5 | 97.5 | 75 | 84.4 | 84.4 |

DF: Discrimination Function
DS: Discrimination Score
FORM 1[(7)] = $MCV^2 \times MCH$
FORM 2[(6)] = MCV/RBC
IDA: Iron Deficiency Anemia
MDHL: Total Hemoglobin in Density
TT: Thalassemia Trait
PV: Predictive Value Furthermore, the extraordinary utility of MDHL becomes clearer when the 3 patients (2 females and 1 male) as indicated in Table 2, who had combined both IDA and β-thal trait (IDA prevailing in 2 and TT dominating in the other) were excluded. The sensitivities, specificities, the PV, negative as well as positive of the determination of the remaining 93 patients, reached 100%. Most importantly, this discriminating effect holds regardless of whether the beta- or alpha-Thalassemia Traits are considered. Thus, MDHL provides an efficacious tool for discriminating between IDA and TT.

It would be considered well within the purview of this invention to program the new useful parameters into the future or even the present generation cell counters since it would be a relatively simple matter to convert them to this MDHL method. This change is expected to advantageously result in considerable economies in the clinical hematological practice, while affording a reliable and rapid diagnosis.

REFERENCES

1) Wintrobe M M: A simple and accurate hematocrit. J Lab Clin Med 15:287, 1929.
2) Maxwell M. Wintrobe: Wintrobe's Clinical Hematology, Lea and Febiger, Philadelphia, London, 1993, Volume 1, Page 8.
3) Ibid., page 18.
4) England J M, Fraser P M: Differentiation of iron-deficiency from thalassemia trait by routine blood-count. Lancet I: 449, Mar. 3, 1973.
5) England J M, Fraser P M: Discrimination between iron-deficiency and heterozygous-thalassemia syndromes in differential diagnosis of microcytosis. Lancet 1: 145, Jan. 20, 1979.
6) Mentzer W C: Differentiation of iron deficiency from thalassemia trait. Lancet I: 882, Apr. 21, 1973.
7) Shine I, Lal, S: Strategy to detect B-thalassemia minor. Lancet I: 692, 1973.
8) Fairbanks V F, Hines J D, Mazza J J, Hocking W G: chapter 2, The Anemias. In: Joseph J. Mazza, Manual of Clinical Hematology. Little, Brown & Co., Boston, New York, Toronto, London. 1995, page 17.
9) Robert C. Weast: CRC-Handbook of Chemistry and Physics, 61st Edition, 1980–1981, CRC Press, Florida. Page F-99.
10) Karl F. Kuhn "Basic Physics a self teaching guide. $2^{nd}$ edition, 1996. John Wiley and Sons Inc., page 65.
11) Mohandas N, Kim Y R, Tycko D H, Orlik J, Wyatt J, Grover W. Accurate and independent measurement of volume and hemoglobin concentration of individual red cells by laser light scattering. Blood 68: 506, 1986.
12) Al-Buhairan, A. Base-line haematological parameters in healthy adult male and female Saudis. Masters Degree Thesis. King Saud University, Riyadh, 1998.
13) Mohandas N, Johnson A, Wyatt J, Croisille L, Reeves J, Tycko D, Grover W. Automated quantitation of cell density distribution and hyperdense cell fraction in RBC disorders. Blood 74: 442, 1989.

What is claimed is:

1. A parameter for discrimination of hypochromic microcytosis (HM) of blood which is defined as a mean density of hemoglobin in one liter of blood (MDHL).

2. The parameter of claim 1, which is calculated from the formula, $$MDHL = MCHD\ (pg/fl) \times RBCC \times 10^{12}\ L,$$

wherein MCHD is a mean cellular hemoglobin density of a single red blood cell, RBCC is a red blood cell count, and the units of MDHL are grams per liter (g/L).

3. The parameter of claim 2, wherein MCHD is defined by the relation, MCH (mean cell hemoglobin, pg) divided by MCV (mean cell volume, fl).

4. A method for characterizing a blood condition of patients suffering from hypochromic microcytosis (HM), which comprises:
   determining a mean density of hemoglobin in one liter of blood (MDHL) in a sample of HM blood as a hematological parameter in a screening test for discriminating between an iron deficiency anemia (IDA) and a Thalassemia Trait (TT).

5. The method of claim 4, wherein the MDHL is the product of a mean cell hemoglobin density (MCHD, pg/fl)

multiplied by a red blood cell count (RBCC)$\times 10^{12}$ L, and wherein MCHD is a red blood cell index, which is calculated from the formula:

$$MCHD = \frac{MCH \text{ (Mean Cell Hemoglobin)}}{MCV \text{ (Mean Cell Volume)}}$$

6. The method of claim 4, wherein the MDHL of HM blood lower than a normal median value indicates an IDA condition; and wherein the MDHL of HM blood higher than the normal median value indicates a TT condition.

7. The method of claim 4 or 6, wherein the TT comprises alpha-thalassemia or beta-thalassemia trait.

* * * * *